United States Patent [19]

Hattori et al.

[11] Patent Number: 4,729,952
[45] Date of Patent: Mar. 8, 1988

[54] PROCESS FOR PRODUCING L-GLUTAMIC ACID BY FERMENTATION

[75] Inventors: Kiyoji Hattori; Yukinobu Kotani; Kuniki Kino, all of Hofu, Japan

[73] Assignee: Kyowa Hakko Kogyo Co., Ltd., Tokyo, Japan

[21] Appl. No.: 582,883

[22] Filed: Feb. 23, 1984

[30] Foreign Application Priority Data

Feb. 25, 1983 [JP] Japan .................................. 58-30480
Sep. 22, 1983 [JP] Japan ................................ 58-174319

[51] Int. Cl.$^4$ ........................ C12P 13/14; C12N 1/20; C12R 1/13; C12R 1/15
[52] U.S. Cl. ................................ 435/110; 435/253; 435/840; 435/843
[58] Field of Search ............... 435/110, 111, 253, 840, 435/843, 172.1

[56] References Cited

U.S. PATENT DOCUMENTS

| | | | |
|---|---|---|---|
| 3,704,205 | 11/1972 | Shiro et al. | 435/843 |
| 3,764,473 | 10/1973 | Tanaka et al. | 435/843 |
| 3,784,446 | 1/1974 | Nishida et al. | 435/843 |
| 4,347,317 | 8/1982 | Yoshimura et al. | 435/840 |
| 4,389,483 | 6/1983 | Hiraga et al. | 435/843 |
| 4,393,135 | 7/1983 | Tsuchida et al. | 435/110 |
| 4,495,283 | 1/1985 | Araki et al. | 435/107 |

FOREIGN PATENT DOCUMENTS

| | | | |
|---|---|---|---|
| 0113569 | 7/1984 | European Pat. Off. | |
| 0117740 | 9/1984 | European Pat. Off. | |
| 0140895 | 11/1981 | Japan | 435/840 |
| 0141788 | 8/1983 | Japan | 435/840 |
| 2056451 | 3/1981 | United Kingdom | |

OTHER PUBLICATIONS

Lehninger, A. L., Biochemistry (1972), Worth Publishing, Inc., pp. 338–339, 378–379, 436.
Chem. Abs., vol. 96, No. 8 (1982), 120905c.

Primary Examiner—John Tarcza
Attorney, Agent, or Firm—Fitzpatrick, Cella, Harper & Scinto

[57] ABSTRACT

A process is disclosed for producing L-glutamic acid, the process involves culturing a microorganism belonging to the genus Corynebacterium or Brevibacterium and having both an ability to produce L-glutamic acid and a resistance to α-naphthoquinoline, an antibiotic inhibiting energy metabolism or a precursor for ubiquinone biosynthesis in a nutrient medium until L-glutamic acid is accumulated in the resulting culture liquor, and recovering the L-glutamic acid therefrom.

6 Claims, No Drawings

PROCESS FOR PRODUCING L-GLUTAMIC ACID BY FERMENTATION

BACKGROUND OF THE INVENTION

The present invention relates to a process for producing L-glutamic acid by fermentation, and more specifically to a process for producing L-glutamic acid by culturing an L-glutamic acid producing mutant microorganism belonging to the genus Corynebacterium or Brevibacterium in a nutrient medium and recovering the L-glutamic acid produced thereby. The microorganisms employed are mutants endowed with a resistance to α-naphthoquinoline, an antibiotic inhibiting energy metabolism or a precursor for ubiquinone biosynthesis.

L-glutamic acid is an important amino acid which is commercially useful as a food additive. Accordingly, it is an object of the present invention to provide an improved process for production of such amino acid on an industrial scale at low cost.

Heretofore, as processes for producing L-glutamic acid by fermentation, there have been known processes of using strains having a nutritional requirement for various compounds, strains having sensitivity to various chemicals, or various chemicals-resistant strains, belonging to the genus Corynebacterium or Brevibacterium.

The production yields of known processes are comparatively low from a commercial application standpoint. Thus, a need exists for a process for producing L-glutamic acid in higher yields at low cost.

As a result of various studies for obtaining strains having an increased L-glutamic acid productivity, it has been found that a strain capable of producing L-glutamic acid belonging to the genus Corynebacterium or Brevibacterium endowed with a resistance to α-naphthoquinoline, an antibiotic inhibiting energy metabolism or a precursor for ubiquinone biosynthesis has a remarkably improved ability to produce L-glutamic acid.

SUMMARY OF THE INVENTION

In accordance with the present invention, L-glutamic acid is produced in high yield by culturing a mutant having an ability to produce L-glutamic acid in a nutrient medium until L-glutamic acid is accumulated in the culture liquor and recovering L-glutamic acid therefrom. The process is characterized by using a mutant belonging to the genus Corynebacterium or Brevibacterium and having a resistance to α-naphthoquinoline, an antibiotic inhibiting energy metabolism or a precursor for ubiquinone biosynthesis.

As used herein the term "antibiotics inhibiting energy metabolism" means that the antibiotics have influences on the electron transport of respiratory chain or oxidative phosphorylation.

Examples of antibiotics include an inhibitor on the electron transport system such as antimycin A, uncoupling agents allowing electron transport to continue but prevent the phosphorylation of ADP to ATP such as gramicidin S, valinomycin, etc., inhibitors of oxidative phosphorylation preventing the ATP-forming mechanism from utilizing the high-energy intermediate or state generated by electron transport such as oligomycin, rutamycin, etc.

Furthermore, as used herein the term "precursors for ubiquinone biosynthesis" means that the precursors are biosynthetic intermediates of ubiquinone which plays an important role in the electron transport of respiratory chain for acquiring the energy.

DESCRIPTION OF THE INVENTION

The microorganism utilized in the present invention is a mutant belonging to the genus Corynebacterium or Brevibacterium which has the ability to produce L-glutamic acid and which is endowed with a resistance to α-naphthoquinoline, an antibiotic inhibiting energy metabolism or a precursor for ubiquinone biosynthesis.

A suitable mutant may be obtained by using a mutant inherently having an ability to produce L-glutamic acid or an improved mutant thereof as a parent strain and imparting a resistance to α-naphthoquinoline, an antibiotic inhibiting energy metabolism, e.g. oligomycin, antimycin A, rutamycin, gramicidin S, valinomycin, etc., or a precursor for ubiquinone synthesis, e.g. o-hydroxycinnamate (o-coumarate) and its fluoride, m-hydroxycinnamate (n-coumarate) and its fluoride, p-hydroxycinnamate (p-coumarate) and its fluoride, phenyl pyruvate, p-hydroxyphenyl pyruvate and its fluoride, phenyl acetate, p-hydroxyphenyl lactate and its fluoride, cinnamate, benzoate, p-hydroxybenzoate and its fluoride and p-hydroxybenzaldehyde and its fluoride.

Alternatively, a suitable mutant may be prepared by a reverse process, i.e. by imparting the above-mentioned ability to produce L-glutamic acid to a mutant resistant to α-naphthoquinoline, an antibiotic inhibiting energy metabolism or a precursor for ubiquinone biosynthesis.

The mutant microorganism useful in carrying out the present invention can be obtained by conventional means such as ultraviolet ray irradiation, X-ray irradiation, radioactive ray irradiation and a treatment with chemical mutagens. A treatment using N-nitro-N'-methyl-N-nitrosoguanidine (hereinafter referred to as NTG) is preferably employed.

Moreover, as the strain used in this invention, a mutant having other properties such as various nutrient requirements, drug resistance, drug sensitivity and drug dependence in addition to the above properties may be employed.

Strains mutated as above mentioned are screened by culturing in a nutrient medium and a strain having the ability to produce L-glutamic acid in greater yields than its parent strain is selected and used in this invention. A specific example of the procedure for obtaining a suitable strain is given in the following description.

PROCEDURE

*Corynebacterium glutamicum* ATCC 13032 is treated with NTG in a conventional manner. A suspension of the treated cells is cultured at 30° C. in an agar medium containing 0.5 g/dl enzyme extract, 0.7 g/dl meat extract, 1 g/dl peptone, 0.3 g/dl NaCl, 2 g/dl agar and 100 μg/ml α-naphthoquinoline, at 30° C.

Among the formed colonies, a culture test of L-glutamic acid is peformed to choose a mutant having excellent productivity.

Thus, L-glutamic acid-producing *Corynebacterium glutamicum* CQ-306 (hereinafter referred to as CQ-306) having a resistance to α-naphthoquinoline is obtained.

In a similar manner, *Brevibacterium lactofermentum* BQ-13 (hereinafter referred to as BQ-13) is obtained from *Brevibacterium lactofermentum* ATCC-13869.

These CQ-306 and BQ-13 strains were deposited with ARS Culture Collection Research Fermentation Laboratory under the Budapest Treaty on July 21, 1983 and assigned the international accession Nos. NRRL B-15531 and NRRL B-15530, respectively.

Also, *Corynebacterium glutamicum* ATCC-13032 or *Brevibacterium lactofermentum* ATCC-13869 is suspended in a M/20 phosphate buffer solution (pH 7.0). To the suspension is added 200 μg/ml NTG and the mixture is maintained to 30° C. for 30 minutes. The treated mutants are collected and washed with the same buffer solution. Then, the mutants are spread on a medium (pH 6.8) comprising 3% glucose, 0.2% urea, 10 ppm each of Fe, Mn and Cu ions, 1 mg/l thiamine hydrochloride, 50 μg/l biotin and 2% agar, and further containing 100 μg/ml oligomycin or 2 mg/ml p-hydroxycinnamate. Culturing is carried out at 30° C. for 2 to 10 days. Among these mutants, those having a remarkably improved ability of producing L-glutamic acid are separated. Typical examples of the oligomycin-resistant strains are *Corynebacterium glutamicum* COM-53 (hereinafter referred to as COM-53) (FERM BP-428) and *Brevibacterium lactofermentum* BOM-419 (hereinafter referred to as BOM-419) (FERM BP-429). Typical examples of p-hydroxycinnamate-resistant strains are *Corynebacterium glutamicum* CPC-8 (hereinafter referred to as CPC-8) (FERM BP-430) and *Brevibacterium lactofermentum* BPC-106 (hereinafter referred to as BPC-106) (FERM BP-431).

The strains COM-53, BOM-419, CPC-8 and BPC-106 were deposited on Feb. 19, 1983 outside the Budapest Treaty with the Fermentation Research Institute, the Agency of Industrial Science and Technology, Japan as FERM P numbers shown below. The deposits were converted into the deposits under the Budapest Treaty, and the corresponding international deposit numbers are shown below.

| Strain | FERM P No. | FERM BP No. |
|---|---|---|
| COM-53 | 6921 | 428 |
| BOM-419 | 6922 | 429 |
| CPC-8 | 6923 | 430 |
| BPC-106 | 6924 | 431 |

Either a synthetic or natural medium may be used as the medium for the present invention, so long as it properly contains a carbon source, nitrogen source, inorganic materials and other necessary nutrients which are assimilable by the strain utilized.

As the carbon source, various carbohydrates such as glucose, fructose, maltose, monnose, glycerol, sucrose, starch, starch hydrolyzate and molasses, sugar alcohols, such as glycerol and sorbitol, organic acids, such as acetic acid, fumaric acid, lactic acid, pyruvic acid, gluconic acid, formic acid, butyric acid and malic acid, lower alcohols such as ethanol and methanol, and hydrocarbons, etc. may be used.

As the nitrogen source, ammonia, inorganic and organic ammonium salts, such as ammonium chloride, ammonium sulfate, ammonium acetate, phosphate, ammonium carbonate and ammonium nitrate, urea, amines, other nitrogen-containing compounds such as peptone, meat extract, yeast extract, corn steep liquor, casein hydrolyzate, acid hydrolyzate of soybean meal, various microbial cells, digest of microbial cells, etc., may be used.

As the inorganic materials, potassium dihydrogen phosphate, dipotassium hydrogen phosphate, magnesium phosphate, magnesium sulfate, sodium chloride, ferrous sulfate, manganese sulfate, copper sulfate, calcium carbonate, etc. are used. Where a microorganism to be used in the present invention requires specific nutrients for growth, an appropriate amount of the nutrients are added to the medium. In some cases, these nutrients are added as components of the natural substances exemplified as the nitrogen source.

Further, the productivity of L-glutamic acid by the present microorganism can be, in some cases, enhanced by adding other various additives, for example, various antibiotics such as streptomycin, penicillin G and rifampicin, antioxidant such as α-tocopherol, surfactants such as polyoxyethylene sorbitan-mono-parmitate, amino acids such as methionine, lysine, cysteine and aspartic acid, biotin, acetic acid, oleic acid, adenine, etc., to the medium.

Culturing is carried out under aerobic conditions, for example, by shaking culture, agitation submerged culture, etc. The temperature for culturing is generally 20°-40° C., and the pH of the medium is in a range of 3 to 9, and is preferably maintained at around neutrality, but culturing can be carried out under conditions which are out of this range so long as the microorganism used can grow. The pH of the medium is adjusted with calcium carbonate, acid or alkali solution, ammonia, pH buffering agent, etc. Usually, after culturing for 1 to 4 days, L-glutamic acid is formed and accumulated in the resulting culture liquor.

After the completion of culturing, precipitates such as cells, are removed from the culture liquor and L-glutamic acid can be recovered from the culture liquor by use of the conventional methods, such as ion-exchange resin treatment, concentration, adsorption and salting-out in combination.

Practice of specific embodiments of the invention is illustrated by the following representative examples.

EXAMPLE 1

As seed strains, 4 strains of *Corynebacterium glutamicum* ATCC-13032, CQ-306 strain, *Brevibacterium lactofermentum* ATCC-13869 and BQ-13 strain are used.

Each of these strains is inoculated into a seed medium (pH 7.2) comprising 4 g/dl glucose, 2 g/dl polypeptone, 0.5 g/dl yeast extract, 0.15 g/dl $KH_2PO_4$, 0.05 g/dl $K_2HPO_4$, 0.05 g/dl $MgSO_4.7H_2O$, 100 μg/ml biotin and 0.3 g/dl urea. Culturing is carried out at 30° C. with shaking for 24 hours. Then, 1 ml of the culture liquor is put into a 300 ml-Erlenmeyer flask containing 20 ml of a fermentation medium having the composition described below. Culturing is carried out at 30° C. with shaking for 3 days.

The results are shown in Table 1.

Composition of Fermentation Medium:

10 g/dl glucose, 0.5 g/dl meat extract, 3 g/dl ammonium sulfate, 0.15 g/dl $KH_2PO_4$, 0.05 g/dl $K_2HPO_4$, 0.05 g/dl $MgSO_4.7H_2O$, 500 μg/l thiamine hydrochloride, 10 mg/l $FeSO_4.7H_2O$, 10 mg/l $MnSO_4.4H_2O$, 1 mg/l $CuSO_4.5H_2O$, 0.5 g/dl urea, 3 g/dl $CaCO_3$ (pH 7.2), sterilized at 120° C. for 10 minutes.

TABLE 1

| Strain | L-Glutamic acid (g/l) | Yield based on Sugar (%) |
|---|---|---|
| ATCC-13032 | 49 | 49 |
| CQ-306 | 59 | 59 |
| ATCC-13869 | 45 | 45 |
| BQ-13 | 55 | 55 |

EXAMPLE 2

The same procedures as described in Example 1 are repeated except that 10 g/dl (calculated as glucose) molasses is used in place of glucose of the fermentation medium and 5 U/ml of penicillin G is added at the initiation of the culturing. The results are shown in Table 2.

TABLE 2

| Strain | L-Glutamic acid (g/l) | Yield based on Sugar (%) |
|---|---|---|
| ATCC-13032 | 46 | 46 |
| CQ-306 | 57 | 57 |
| ATCC-13869 | 41 | 41 |
| BQ-13 | 52 | 52 |

EXAMPLE 3

As seed strains, four strains of *Corynebacterium glutamicum* ATCC-13032 and COM-53 and *Brevibacterium lactofermentum* ATCC-13869 and BOM-419 are used.

As a seed medium, the medium (pH 7.2) having a composition of 4% glucose, 2% polypeptone, 0.5% yeast extract, 0.15% $KH_2PO_4$, 0.05% $K_2HPO_4$, 0.05% $MgSO_4.7H_2O$, 100 μg/l biotin and 0.3% urea, which has been sterilized at 120° C. for 10 minutes, is employed. The strains described above are cultured at 30° C. with shaking for 24 hours. Then, 1 ml of the culture liquor is inoculated into 20 ml of a fermentation medium described below which is charged in a 300 ml-Erlenmeyer flask. Culturing is carried out at 30° C. with shaking for 3 days. The results are shown in Table 3.

Composition of Fermentation Medium:

10% glucose, 0.5% meat extract, 3% ammonium sulfate, 0.15% $KH_2PO_4$, 0.05% $K_2HPO_4$, 0.05% $MgSO_4.7H_2O$, 500 μg/l of thiamine hydrochloride, 10 mg/l $FeSO_4.7H_2O$, 10 mg/l $MnSO_4.6H_2O$, 1 mg/l $CuSO_4.5H_2O$, 0.5% urea, 3% $CaCO_3$ (pH 7.2), sterilized at 120° C. for 10 minutes.

TABLE 3

| Strain | L-Glutamic acid (g/l) | Yield Based on Sugar (%) |
|---|---|---|
| ATCC-13032 | 49 | 49 |
| COM-53 | 55 | 55 |
| ATCC-13869 | 45 | 45 |
| BOM-419 | 53 | 53 |

EXAMPLE 4

The same procedures as described in Example 3 are repeated except that 10% (calculated as glucose) molasses is used in place of glucose as the fermentation medium in Example 3 and penicillin G solution is added to make a final concentration of 5 U/ml at the initiation of the culturing. The results are shown in Table 4.

TABLE 4

| Strain | L-Glutamic acid (g/l) | Yield Based on Sugar (%) |
|---|---|---|
| ATCC-13032 | 46 | 46 |
| COM-53 | 52 | 52 |
| ATCC-13869 | 41 | 41 |
| BOM-419 | 47 | 47 |

EXAMPLE 5

The same procedures as described in Example 3 are repeated except that 4 strains of *Corynebacterium glutamicum* ATCC-13032, CPC-8, *Brevibacterium lactofermentum* ATCC-13869 and BPC-106 are used as seed strains. The results are shown in Table 5.

TABLE 5

| Strain | L-Glutamic acid (g/l) | Yield Based on Sugar (%) |
|---|---|---|
| ATCC-13032 | 49 | 49 |
| CPC-8 | 58 | 58 |
| ATCC-13869 | 45 | 45 |
| BPC-106 | 53 | 53 |

EXAMPLE 6

The same procedures as described in Example 3 are repeated except that 10% (calculated as glucose) molasses is used in place of glucose in the fermentation medium of Example 3 and penicillin G solution is added to make a final concentration of 5 U/ml at the initiation of the culturing. The results are shown in Table 6.

TABLE 6

| Strain | L-Glutamic acid (g/l) | Yield Based on Sugar (%) |
|---|---|---|
| ATCC-13032 | 46 | 46 |
| CPC-8 | 54 | 54 |
| ATCC-13869 | 41 | 41 |
| BPC-106 | 49 | 49 |

What is claimed is:

1. A process for producing L-glutamic acid, which comprises culturing a microorganism belonging to the genus Corynebacterium or Brevibacterium which has both an ability to produce L-glutamic acid and a resistance to 100 μg/ml α-naphthoquinoline, 100 μg/ml oligomycin, or 2 mg/ml p-hydroxycinnamate in a nutrient medium until L-glutamic acid is accumulated in the culture liquor, and thereafter recovering the L-glutamic acid therefrom.

2. The process according to claim 1, wherein said microorganism belongs to the species *Corynebacterium glutamicum* or *Brevibacterium lactofermentum*.

3. The process according to claim 1, wherein said microorganism is *Corynebacterium glutamicum* CQ-306, NRRL B-15531, *Corynebacterium glutamicum* COM-53, FERM BP-428, *Corynebacterium glutamicum* CPC-8, FERM BP-430, *Brevibacterium lactofermentum* BQ-13, NRRL B-15530, *Brevibacterium lactofermentum* BOM-419, FERM BP-429 or *Brevibacterium lactofermentum* BPC-106, FERM BP-431.

4. The process according to claim 1, wherein said culturing is conducted at 20° to 40° C. for 1 to 4 days.

5. A biologically pure culture of the microorganism *Corynebacterium glutamicum* having the identifying characteristics of a member selected from a group consisting of NRRL B-15531, FERM BP-428 and FERM BP-430 which culture possesses the ability to produce L-glutamic acid.

6. A biologically pure culture of the microorganism *Brevibacterium lactofermentum* having the identifying characteristics of a member selected from a group consisting of NRRL B-15530, FERM BP-429 and FERM BP-431 which culture possesses the ability to produce L-glutamic acid.

* * * * *